US009533239B2

(12) United States Patent
Pennino

(10) Patent No.: US 9,533,239 B2
(45) Date of Patent: Jan. 3, 2017

(54) CARBON DIOXIDE STRIPPING UREA PLANT WITH A NATURAL-CIRCULATION SYNTHESIS LOOP AND A METHOD FOR RETROFITTING SUCH PLANT

(75) Inventor: Lorenzo Pennino, Lugano-Pregassona (CH)

(73) Assignee: Casale SA (CH)

( * ) Notice: Subject to any disclaimer, the term of this patent is extended or adjusted under 35 U.S.C. 154(b) by 486 days.

(21) Appl. No.: 14/343,645

(22) PCT Filed: Apr. 25, 2012

(86) PCT No.: PCT/EP2012/057531
§ 371 (c)(1),
(2), (4) Date: Mar. 7, 2014

(87) PCT Pub. No.: WO2013/034319
PCT Pub. Date: Mar. 14, 2013

(65) Prior Publication Data
US 2014/0227139 A1 Aug. 14, 2014

(30) Foreign Application Priority Data
Sep. 9, 2011 (EP) .................................. 11180730

(51) Int. Cl.
*B01J 19/00* (2006.01)
*C07C 273/04* (2006.01)
*B01D 3/00* (2006.01)

(52) U.S. Cl.
CPC .............. *B01D 3/009* (2013.01); *B01J 19/002* (2013.01); *C07C 273/04* (2013.01);
(Continued)

(58) Field of Classification Search
CPC .................... B01J 19/0006; B01J 2208/00008; B01J 2219/00049; B01J 8/001; B01J 19/002; B01D 3/009; C07C 273/04
(Continued)

(56) References Cited

U.S. PATENT DOCUMENTS 4,006,634 A * 2/1977 Billette ...................... G01F 1/42
73/861.53
4,083,245 A * 4/1978 Osborn ...................... G01F 1/42
73/861.53
(Continued)

FOREIGN PATENT DOCUMENTS

EP 0329215 A1 8/1989
EP 2123634 A1 11/2009
EP 2199279 A1 6/2010

OTHER PUBLICATIONS

International Search Report issued in connection with PCT/EP2012/057531.
(Continued)

*Primary Examiner* — Walter D Griffin
*Assistant Examiner* — Huy-Tram Nguyen
(74) *Attorney, Agent, or Firm* — Akerman LLP

(57) ABSTRACT

A plant for synthesis of urea with a CO2-stripping process, comprising a natural-circulation synthesis loop, said loop including at least a urea reactor (1), a carbon dioxide stripper (2) and a condenser (3), said reactor, stripper and condenser operating substantially at the same elevated pressure, said loop comprising also a reactor effluent flow line (5), connecting said urea reactor to said stripper, which comprises means (15) for directly or indirectly detecting the flow rate and/or the direction of the flow through said reactor effluent flow line (5).

12 Claims, 1 Drawing Sheet

(52) U.S. Cl.
CPC .............. *B01J 2219/00006* (2013.01); *B01J 2219/0027* (2013.01); *B01J 2219/00162* (2013.01); *B01J 2219/00164* (2013.01); *B01J 2219/00182* (2013.01); *B01J 2219/00202* (2013.01); *B01J 2219/00225* (2013.01); *Y02P 20/142* (2015.11); *Y10T 29/49716* (2015.01)

(58) Field of Classification Search
USPC ........................................................ 422/105
See application file for complete search history.

(56) References Cited

U.S. PATENT DOCUMENTS

| | | | |
|---|---|---|---|
| 8,383,856 B2* | 2/2013 | Romiti | C07C 273/04 423/365 |
| 2009/0090504 A1* | 4/2009 | Weightman | E21B 43/26 166/250.01 |

OTHER PUBLICATIONS

International Preliminary Report on Patentability issued in connection with PCT/EP2012/057531.
Meessen, Jozef H., "Urea, Ullmann's Encyclopedia of Industrial Chemistry", Oct. 15, 2010, Wiley-VCH Verlag GmbH & Co., pp. 657-695.
"BHDT Installation", http://www.ureaworld.cn/thi__comp__news__con.asp?wenzhangid=14&wordid=41, Jun. 18, 2010.

* cited by examiner

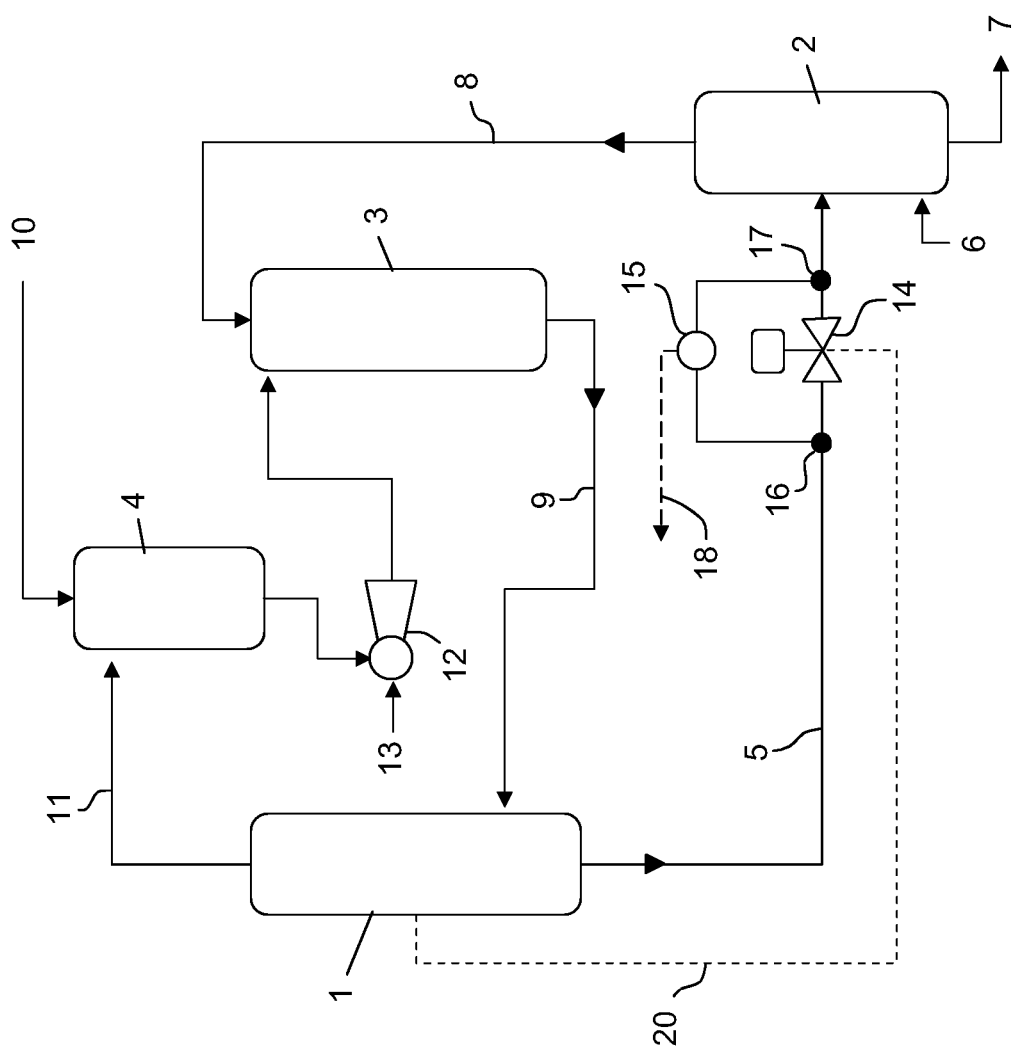

CARBON DIOXIDE STRIPPING UREA PLANT WITH A NATURAL-CIRCULATION SYNTHESIS LOOP AND A METHOD FOR RETROFITTING SUCH PLANT

This application is a national phase of PCT/EP2012/057531, filed Apr. 25, 2012, and claims priority to EP 11180730.1, filed Sep. 9, 2011, the entire contents of both of which are hereby incorporated by reference.

FIELD OF THE INVENTION

The present invention relates to urea plants. More in detail, the invention relates to an improvement for CO2-stripping urea plants with a natural circulation of the high-pressure synthesis loop.

PRIOR ART

The CO2-stripping urea process is known in the art. An introduction of the CO2-stripping process can be found in the Ullmann's Encyclopedia of Industrial Chemistry, $5^{th}$ revision, vol. A27, par. 3.3.2. The synthesis section of a plant running with the CO2-stripping process comprises basically: a urea reactor; a stripper; a carbamate condenser; a reactor off-gas scrubber. Said reactor, stripper, condenser and scrubber are part of a so-called high-pressure synthesis loop. The pressure in the synthesis loop is usually around 140-150 bar; the loop is substantially isobaric, i.e. the pressure inside the above said equipments is substantially the same apart from small deviations and/or relatively small pressure losses through pipes, valves, etc.

The term natural-circulation loop denotes an isobaric synthesis loop where circulation of the process streams is governed by gravity and/or difference of density, contrary to a forced circulation loop where circulation is effected by a machine such as an ejector or a pump and the loop is non-isobaric. Forced circulation is used for example in self-stripping or ammonia-stripping plants.

In a natural-circulation loop a different density between one vessel and another is determined mainly by a different composition or gas/liquid ratio. To provide a driving force by gravity, the equipments of the loop may be placed at different heights, for example installing the reactor above the stripper. In particular, a driving force is given by the liquid level in the reactor. The liquid level in the reactor is governed with a valve placed on the effluent reactor line, going from reactor to stripper. Said valve is termed reactor level valve and indirectly controls also the overall circulation in the loop.

A natural-circulation CO2-stripping loop has a drawback in that unexpected change of liquid/gas ratio or density may reduce the driving force and hence the flow rate or, in the worst case, may reverse the flow. For example if the liquid level in the reactor is low, it may happen that the pressure in the stripper is sufficient to start a reverse flow from stripper to reactor. A reversal of the flow will cause a sudden increase of the loop pressure, well beyond the nominal 140-150 bar. A risk exists that said increase of loop pressure causes the opening of a safety valve, thus releasing a great amount of ammonia in atmosphere and plant shut down. This event, though rare, is possible. The above risk is greater during the startup phase.

SUMMARY OF THE INVENTION

The invention aims to prevent the above risk of flow reversal in a natural-circulation, CO2-stripping urea synthesis loop. The invention also aims to provide a more accurate control of the flow which is established in a natural-circulation loop of a CO2-stripping plant.

The proposed solution is a plant for synthesis of urea with a CO2-stripping process, comprising a natural-circulation synthesis loop, said loop including at least a urea reactor, a stripper and a condenser, said reactor, stripper and condenser operating substantially at the same elevated pressure, said loop comprising also a reactor effluent flow line, connecting said urea reactor to said stripper, characterized in that the plant comprises means for directly or indirect detecting the flow rate and/or the direction of the flow in said reactor effluent flow line.

According to the embodiments of the invention, the above means can be arranged to measure the flow rate (mass or volume over time) and/or just the direction of the flow (i.e. whether from reactor to stripper, or vice-versa) in the reactor effluent line. In some embodiments said means include a flow meter.

A preferred embodiment of the invention comprises a differential pressure sensor between at least two selected points of said reactor effluent flow line. The term delta-p is short for difference of pressure.

More preferably, said selected points comprises a first point of measure which is upstream a reactor level valve, and a second point of measure which is downstream said valve. Following this embodiment, a positive delta-p across said valve will denote that the loop is under normal operation, namely that urea solution is flowing from reactor to stripper as usual; a negative delta-p across the valve will denote the unwanted, dangerous condition of reverse flow, namely from stripper to reactor. This embodiment with sensing of delta-p across the reactor level valve is particularly preferred because it makes possible to predict the risk of a reverse flow even before a startup of the plant, when the valve is closed and there is no flow to measure in the effluent line.

Detection of a reverse flow rate or of the approaching of this condition, e.g. of flow rate falling below a given threshold, may either generate an alarm signal for human intervention, or an automated intervention of the control system.

Optionally, a measure of the flow rate, for example the magnitude of the positive delta-p in the above example, can be used to monitor the operation of the loop; the magnitude of flow rate in the reactor effluent line, in some embodiments, is fed to the control system of the plant, which is for example a distributed control system (DCS). Hence the control system can take advantage of this measure in order to maintain stable operation of the loop or during startups.

Though the above delta-p measure is preferred, other embodiments of the detecting means are possible. Another embodiment of the invention, for example, provides an ultrasonic flow meter installed on the reactor effluent flow line. More preferably said flow-meter is a non-intrusive flow meter, to avoid contact with the aggressive urea solution. For example a clamp-on ultrasonic flow meter can be used to carry out the invention.

The invention hence provides a method for controlling a CO2-stripping process where urea is produced in a natural-circulation synthesis loop including at least a urea reactor, a carbon dioxide stripper and a condenser, said method comprising at least the steps of:

detecting the magnitude and/or the sense of flow rate in reactor effluent flow line, which under design operation delivers a urea solution from reactor to stripper, sending an alarm signal when the sense of said flow rate is reversed or the magnitude of flow rate falls below a threshold value, or feeding the measured flow rate through said line to an automated control system of the process.

The invention is applicable to all kinds of CO2-stripping urea plants with natural-circulation loop. As a non limitative example, plants to which the invention is applicable include loops with one or more reactors, condensers or strippers; plants where condensation in the high-pressure condenser is effected partially or totally; embodiments where the overhead gas flow from the stripper is split between the reactor and the condenser.

Another aspect of the invention is the retrofitting of an existing urea plant, by adding the above means for direct or indirect detection of the rate and/or sense of flow in the reactor effluent line. Preferably a delta-p sensor is added with a point of measure upstream the reactor level valve, and another point of measure downstream said valve.

The invention allows avoiding in a safe manner the risk of reverse flow in the loop. The invention gives also an advantage during the start-up phase, when the pressure inside the main equipments may deviate from nominal values, sometimes in unexpected manner, and hence, the risk of a reverse flow is higher. By checking the flow rate in the effluent line, from reactor to stripper, or by checking the differential pressure across the valve, the invention ensures that reverse start is avoided and loop circulation is established in the right sense.

Some embodiments of the invention provide also a measure of the flow rate. Said measure can be used for a more accurate control of the process.

A further advantage is the low cost and easy implementation, especially for existing plants. The above advantages are reached with the addition of a sensor, such as the disclosed delta-p sensor or flow meter, without any modification of the main pressure vessels of the loop. This is a considerable advantage when revamping a urea plant, because no sensor means are to be added to the main vessels of the plant, such as reactor, stripper and condenser.

The features and advantages of the invention shall become clearer from the following description of a preferred embodiment, with reference to the attached FIG. 1.

DETAILED DESCRIPTION OF A PREFERRED EMBODIMENT

FIG. 1 is a simplified diagram of the synthesis loop of a CO2-stripping urea plant. The diagram is simplified and some items such as valves, pumps and auxiliaries are not shown for the sake of simplicity.

The loop comprises a urea reactor 1, a high-pressure stripper 2, a high-pressure condenser 3 and a high-pressure scrubber 4. In some embodiments, the loop may comprise more than one vessel for reaction, condensation or stripping, e.g. two condensers or two strippers. The urea solution produced in the reactor 1 and containing unconverted carbamate is directed to stripper 2 via the effluent flow line 5. Ammonia and carbon dioxide are stripped off the solution with the help of the fresh carbon dioxide feed 6. Concentrated urea solution 7 leaves the stripper 2 and is directed to a urea recovery section (not shown). The gaseous flow 8 leaving the stripper and containing ammonia and carbon dioxide is condensed in the condenser 3 and condensate 9 is sent back to reactor 1.

A low-pressure carbamate solution 10 separated in the recovery section is scrubbed in the high-pressure 4 with overhead vapors 11 leaving the urea reactor, and then sent to the condenser 3 via an ejector 12. The ejector 12 is driven by the ammonia feed 13.

The above features are known in the art and different implementations are possible. For example condensation in the condenser 3 may be partial or total; in case of partial condensation, the remaining gases are condensed in the reactor 1; in case of total condensation in the condenser 3, a gaseous feed of CO2 to reactor 1 is provided, e.g. splitting the main feed 6 into two lines, one to the stripper and the other to the reactor. Further embodiments include that the flow 8 is split into two parts, one part being sent to the reactor and the other part being sent to the condenser. These embodiments are cited as non-limitative examples of application of the invention.

Circulation in the loop 1→2→3, that is inside flow lines 5→8→9, takes place naturally, being governed by gravity and by different values of the overall density inside the pressure vessels of the reactor, stripper and condenser. To this purpose, the stripper is usually below the reactor. A relevant driving force, in particular is given by the liquid level in the reactor, which is controlled by a valve 14. Said valve 14 receives a signal 20 from a sensor detecting the liquid level inside reactor 1, and operates by maintaining said liquid level within a desired range. It can be understood that the opening angle of said valve, introducing a certain pressure drop in the line 5, controls both the liquid level inside the reactor 1 and the flow rate in the line 5, which means that said valve 14 ultimately controls the overall circulation in the loop.

The nominal flow through line 5 goes from reactor 1 to stripper 2 as shown by the arrows in FIG. 1.

In the embodiment of FIG. 1, said line 5 comprises a differential pressure sensor 15 which is mounted across said valve 14. The sensor 15 is sensitive to the difference of pressure between a first point of measure 16 which is upstream the valve 14, and a second point of measure 17 which is downstream the valve 14. Preferably said points 16 and 17 are close to the valve, so that they have the same height and the measure of delta-p is not affected by one of the points of measure being above or below the other.

The delta-p sensed by the sensor 15 is related to the flow rate [kg/s or m3/s] through the line 5. The delta-p is calculated as pressure in point 16 minus pressure in point 17 ($p_{16} - p_{17}$). It can be noted that:
said delta-p>0 means regular flow from reactor 1 to stripper 2,
said delta-p<0 means reverse flow stripper 2 to reactor 1.

Hence the sensor 15 makes available a signal 18 which is related to the current flow rate in the line or, in some embodiments, is a flag signal for triggering an alarm when the delta-p is negative (reverse flow) or when the delta-p is lower than expected. This signal is useful especially when the valve 14 is closed, before a start up. In such a condition, there is no current flowing in line 5, but detection of the pressure on both sides of the valve 14 allows predict the direction of the flow when the valve will open, and then allows prevention of a reverse start-up.

In other embodiments, the delta-p measure can be taken between two generic points of the line 5, for example a first point closer to the reactor 1 and a second point closer to the stripper 2. As apparent, a positive delta-p will indicate regular flow while a negative delta-p will indicate that pressure is greater near the stripper, i.e. that circulation is reversed, or a low delta-p will indicate that the system is approaching the danger of flow reversal.

In some embodiments of the invention, said signal 18 is fed to a control system of the plant. In this way, the control system is able to monitor the flow rate in line 5 and, indirectly, also the variations of density or gas/liquid ratio inside the equipments of the loop.

The invention is also applicable to retrofitting of an existing urea plant. Referring again to FIG. 1, the invention can be carried out by adding the delta-p sensor 15 for measuring the difference of pressure between points 16, 17 across the existing valve 14.

The invention claimed is:

1. A plant for synthesis of urea with a carbon dioxide stripping process, comprising:
   a natural-circulation synthesis loop, said natural-circulation synthesis loop including at least a urea reactor, a stripper and a condenser, said urea reactor, stripper and condenser operating substantially at the same elevated pressure, said natural-circulation synthesis loop comprising also a reactor effluent flow line, connecting said urea reactor to said stripper; and,
   means for directly or indirectly detecting a flow rate and/or a direction of flow in said reactor effluent flow line.

2. The plant according to claim 1, said means being sensitive to difference between pressure in a first point of measure of said reactor effluent flow line and pressure in a second point of measure of said reactor effluent flow line.

3. The plant according to claim 2, said first point of measure being upstream a valve which is provided on the reactor effluent flow line for control of a liquid level in said urea reactor, and said second point of measure being downstream of said valve.

4. The plant according to claim 2, said means comprising a differential pressure sensor connected to said first point of measure and said second point of measure.

5. The plant according to claim 1, said means comprising a flow meter.

6. The plant according to claim 1, said means providing a signal which is related to the flow rate in said reactor effluent flow line.

7. The plant according to claim 1, said means providing a signal which is a flag signal, said flag signal having a first status when the flow rate in said reactor effluent flow line is within a normal operation range, and said signal changing to a second status when the direction of said flow rate is reversed or when the flow rate falls below a threshold value.

8. The plant according to claim 6, said signal being an alarm signal which is activated when the direction of the flow in the reactor effluent flow line is reversed, or when the flow rate in said line falls below a threshold value.

9. The plant according to claim 2, said means providing an alarm signal when said difference of pressure is deviating from normal valves, approaching zero or negative values.

10. A method for retrofitting a $CO_2$-stripping urea plant, said plant comprising a natural-circulation synthesis loop, said natural-circulation synthesis loop including at least a urea reactor, a carbon dioxide stripper and a condenser, said urea reactor, stripper and condenser operating substantially at the same elevated pressure, said natural-circulation synthesis loop comprising also a reactor effluent flow line (5), connecting said urea reactor to said stripper, the method comprises a step of
   adding means for directly or indirectly detecting a flow rate and/or a direction of flow in said reactor effluent flow line.

11. The method according to claim 10, wherein said reactor effluent flow line comprises a valve for controlling a liquid level in the urea reactor, the method comprising adding a differential pressure sensor, said differential pressure sensor being arranged to detect the difference between pressure in a first point of the reactor effluent flow line upstream of said valve, and a second point of the same line downstream of said valve.

12. The method according to claim 10, comprising installing an alarm which is activated when said means detect a reverse flow in the natural-circulation synthesis loop, or when said means detect the flow rate in the natural-circulation synthesis loop falling below a threshold value.

* * * * *